United States Patent [19]

Flegler

[11] Patent Number: 4,670,402
[45] Date of Patent: Jun. 2, 1987

[54] USE OF BENZIMIDAZOLE DERIVATIVES FOR THE DETECTION OF BLOOD AND OTHER PEROXIDATICALLY ACTIVE SUBSTANCES IN BODY FLUIDS AND EXCRETION PRODUCTS

[75] Inventor: Karl-Heinz Flegler, Kreuzau, Fed. Rep. of Germany

[73] Assignee: Macherey-Nagel & Co.-Chemikalienhandel, Duren, Fed. Rep. of Germany

[21] Appl. No.: 815,199

[22] Filed: Dec. 27, 1985

Related U.S. Application Data

[63] Continuation of Ser. No. 517,293, Jul. 26, 1983, abandoned.

Foreign Application Priority Data

Jul. 26, 1982 [DE] Fed. Rep. of Germany ....... 3227893

[51] Int. Cl.$^4$ .................... G01N 33/52; G01N 33/72
[52] U.S. Cl. ......................... 436/66; 422/56; 436/904
[58] Field of Search .......... 436/66, 135, 904; 422/56, 57; 435/28, 805

[56] References Cited

U.S. PATENT DOCUMENTS 3,917,452 11/1975 Rittersdorf et al. ............. 435/28 X
4,278,439 7/1981 White ............................ 422/56 X

FOREIGN PATENT DOCUMENTS 1131108 9/1982 Canada ........................... 435/28
2926271 1/1981 Fed. Rep. of Germany ........ 435/28

OTHER PUBLICATIONS

Claiborne et al., Biochemistry, vol. 18, No. 11, 1979, pp. 2329-2335.

Primary Examiner—Arnold Turk

[57] ABSTRACT

The invention relates to the use of a compound of the chemical formula:

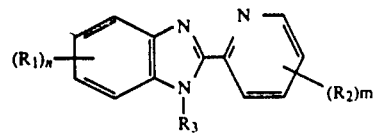

in which:
R$_1$ and R$_2$ are the same or different and represent hydrogen, halogen, and a lower alkyl or alkoxy group containing 1 to 4 carbon atoms, a (C$_1$–C$_4$)-dialkylamino group, an acetylamino group, a nitro group or an aromatic group which may be substituted or anellated;
n is an integer from 1 to 4, preferably 1 or 2;
m is likewise an integer from 1 to 4, preferably 1 or 2; and
R$_3$ is hydrogen, a lower alkyl group with 1 to 4, preferably 1 or 2 carbon atoms, a lower acyl radical, preferably an acetyl radical, or a cyanoalkyl radical, preferably a cyanoethyl radical, or a salt of these compounds;

in a medium for the detection of blood and other peroxidatively active substances in body fluids and excretion products, more particularly on an absorbent carrier together with a chromogen, an organic hydroperoxide as an oxidizing agent, a surface-active agent as well as, if necessary, other auxiliary agents such as thickeners, stabilizers, pigments, a buffer system and/or complex-forming agents.

2 Claims, No Drawings

USE OF BENZIMIDAZOLE DERIVATIVES FOR THE DETECTION OF BLOOD AND OTHER PEROXIDATICALLY ACTIVE SUBSTANCES IN BODY FLUIDS AND EXCRETION PRODUCTS

This application is a continuation of application Ser. No. 517,293, filed July 26, 1983, now abandoned.

BACKGROUND OF THE INVENTION

In connection with the early diagnosis of lesions of the urinary tract, e.g., in the search for neoplasms and stone formation in the kidney and urogenital region, microhematurias have assumed ever increasing importance. Test strips which take advantage of the pseudoperoxidative activity of hemoglobin for the test reaction have proved to be most suitable as a mass screening test and, hence, are equally suitable for the detection of free hemoglobin of already lyzed erythrocytes and for intact erythrocytes (with the lysis occurring on the test field).

Diagnostic agents, more particularly in the form of test strips, for the detection of microhematurias are old in the art. Usually, they consist of an absorbent carrier made from fibrous or non-woven material, in the simplest case, filter paper, and which is impregnated with the detection reagents. The essential components of the detection reagent are a chromogen as an indicator, an oxidizing agent for the indicator, usually a hydroperoxide and an activator, sometimes also called a sensitizer or an accelerator, which increases the sensitivity of the detection. As a rule, other components are, apart from a surface-active agent (wetting agent), thickening agents which prevent the bleeding of the wetted test field, pigments, complex-forming agents and/or other stabilizers for chromogen and/or hydroperoxide.

Various compounds containing aromatically bonded nitrogen have already been proposed as activators to increase test sensitivity. Quinoline derivatives are described in DE-AS Nos. 12 42 905, DE-AS 22 35 152, DE-AS 26 40 211, isoquinoline derivatives in DE-AS 25 48 279, thiazole derivatives in DE-OS No. 26 52 545, and certain pyridine derivatives in DE-OS No. 23 63 344. In Published European Patent Application No. 0 021 407 substituted or condensated pyridines, preferably azafluorene or indenopyridine, are mentioned as activators or accelerators.

DESCRIPTION OF THE INVENTION

The present invention relates to the use of benzimidazole derivatives in methods for the detection of blood and other peroxidatically active substances in body fluids and excretion products, and more particularly as a diagnostic agent in the form of a test paper.

It has surprisingly been found that, apart from the above mentioned known compounds, benzimidazole derivatives are most suitable as activators. Certain benzimidazole derivatives according to the general formula below lead to an increase of stability and activity.

Therefore, the object of the invention is the use of a compound of the chemical formula:

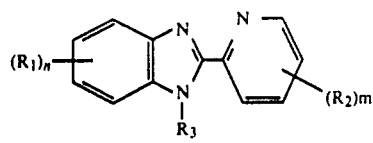

in which:
R$_1$ and R$_2$ are the same or different and represent hydrogen, halogen, a lower alkyl or alkoxy group containing 1 to 4 carbon atoms, a (C$_1$-C$_4$)-dialkylamino group, an acetylamino group, a nitro group or an aromatic substance which may be substituted or anellated;
n is an integer from 1 to 4, preferably 1 or 2;
m is an integer from 1 to 4, preferably 1 to 2, and
R$_3$ is hydrogen, a lower alkyl group with 1 to 4, preferably 1 or 2 carbon atoms, a lower acyl radical, preferably an acetyl radical, or a cyanoalkyl radical, preferably a cyanoethyl radical, or a salt of these compounds;

in a medium for the detection of blood and other peroxidatively active substances in body fluids and excretion products, more particularly on an absorbent carrier together with a chromogen, an organic hydroperoxide as an oxidizing agent, a surface-active agent as well as, if necessary, other auxiliary agents such as thickeners, stabilizers, pigments, a buffer system and/or complex-forming agents.

Furthermore, the object of the invention is a diagnostic agent, more particularly a quick diagnostic agent in the form of a test strip consisting of a carrier, a chromogen, a hydroperoxide, a surface-active agent, an activator, if necessary a buffer system, as well as other auxiliary agents such as thickeners, pigments or complex-forming agents, which is characterized by the fact that the activator is a compound of the general formula indicated above.

The 2-(2-pyridyl)-benzimidazoles of the general formula are known compounds. Their preparation is, for example, described in the following references:
V. J. Cohen, J. Heterocycl. Chem. 16, 13 (1979)
A. Bistrzycki, A. Lecco, Helv. chim. Acta 4, 425 (1921)
D. Jerchel, H. Fischer, M. Kracht, Liebigs An.. 575, 162 (1952)
J. Hall, D. R. Kamm, J. Org. Chem. 30 (6), 2092 (1965)
F. H. Case, J. Heterocycl. Chem. 4, 157 (1967)
M. Ichikawa et al., Chem. Pharm. Bull 25(2), 358 (1977) CA 87, 23155 q
M. Ichikawa, Org. Prep. Proced. Int. 10(5), 205 (1978) CA 89, 179 920 n
R. D. Haugwitz et al., J. Med. Chem. 22, 1113 (1979) CA 91, 211 323 z
M. Ichikawa, Chem. Pharm. Bull. 27(5), 1255 (1979) CA 91, 211 323 z According to the invention, while a number of chromogens are known in the art preferably o-tolidine, dianisidine, guaiacol and tetraalkylbenzidine are used as chromogens.

Among organic hydroperoxides known in the art, diisopropylhydroperoxide, 2,5-dimethylhexane-2,5-dihydroperoxide and cumolhydroperoxide can be used.

All systems are suitable for use as buffers which, following immersion in the fluid to be examined, ensure a pH value of 4 to 7, preferably 5 to 6.

Among the known surface active agents, the preferred surface-active agents (wetting agents) are sodium lauryl sulfate, dioctyl sodium sulphosuccinate, the sodium salt of dodecylbenzenesulphonic acid, the sodium salt of N-dodecanol-N-methylglycine or polyethylenelaurylether.

Among others, gelatin, gum arabic and polyvinylpyrrolidone can be used as thickeners. In addition, the diagnostic agent may also include pigments as well as complex-forming agents. Other stabilizers for the hydroperoxide and/or the chromogen may also be present.

The diagnostic agent is usually prepared by impregnating an absorbent carrier such as filter paper, a cellulose tissue or a tissue of synthetic fibers in a single solution of the components or in at least two solutions and thereafter drying the carrier. In the case of a multistage impregnation the carrier is dried after each impregnation.

The invention is illustrated by the following examples which are to be considered illustrative rather than limiting:

EXAMPLE 1

A solution is prepared from the following components:
Solution I:
  5 g gelatin
  0.6 g o-tolidine
  0.07 g tartrazine
  0.5 g ethylenedinitrilotetraacetic acid tetrasodium salt
  0.2 g dodecylhydrogen sulphate sodium salt
  0.2 g 2-(2-pyridyl)-benzimidazole
  70 ml aqueous citrate buffer pH 5.5 (containing: 6.8 g citric acid, 3.1 g sodium hydroxide)
  30 ml ethanol Filter paper MN 818 is impregnated with the above solution and dried at approximately 70° C. The resultant pretreated paper is then post-impregnated with the following solution and dried at approximately 50° C.:
Solution II:
  3.5 g diisopropylhydroperoxide
  100 ml toluene To prepare the testing agent, the resulting yellow test paper is fixed on a polyester strip in 5×6 mm test zones by means of suitable adhesives. The test zone discolors into green to blue-green within 30 seconds when dipped in urine containing blood. Intact erythrocytes are indicated by a dot-like discoloration, whereas free hemoglobin or myoglobin colors the paper uniformly green. The sensitivity of the test zone is 3 to 5 erythrocytes per μl or the corresponding amount of hemoglobin or myoglobin.

EXAMPLE 2

Filter paper MN 818 is impregnated according to Example 1 with the following solutions one after the other and dried:
Solution II:
  7 g gelatin
  2 g dioctylsodiumsulphosuccinate
  0.1 g ethylenedinitrilotetra acetic acid sodium salt
  1.6 g 2,5-dimethylhexane-2,5-dihydroperoxide
  0.07 g tartrazine
  0.2 g 2-(2-pyridyl)-benzimidazole
  35 ml aqueous citrate buffer pH 5.25 (per liter 96 g NaOH and 253 g citric acid)
  30 ml ethanol
  100 ml distilled water
Solution II:
  0.5 g 0-tolidine
  82 ml ethanol
  18 ml toluene Similarly, instead of 2-(2-pyridyl)-benzimidazole the following compounds can also be used:
  (a) 5-(6)-methyl-2-(2-pyridyl)-benzimidazole
  (b) 4,5-dimethyl-2-(2-pyridyl)-benzimidazole
  (c) 5-(6)-nitro-2-(2-pyridyl)-benzimidazole.

The resulting test papers discolor into green to blue-green upon dipping in blood-containing urine.

EXAMPLE 3

Filter paper MN 215 is impregnated with the following solution and dried at about 70° C.:
  7.8 g tri-sodium citrate
  1.5 g citric acid
  7 g polyvinylpyrrolidone
  2 g dioctylsodiumsulphosuccinate
  0.3 g dodecylhydrogensulphate sodium salt
  0.06 g tartrazine
  0.1 g ethylenedinitrilotetra acetic acid disodium salt
  0.2 g 2-(2-pyridyl)-benzimidazole
  0.5 g 3,3',5,5'-tetramethylbenzidine
  10 ml cumolhydroperoxide
  50 ml distilled water
  50 ml methanol The resulting test paper, which reacts with the same sensitivity as the test paper described in Example 1, is additionally distinguished by a high stability in storage.

EXAMPLE 4

Filter paper MN 215 is impregnated according to Example 1 with the following solutions one after the other and dried:
Solution I:
  4 g gelatin
  0.5 g 3,3',5,5'-tetramethylbenzidine
  0.1 g dodecylhydrogensulphate sodium salt
  0.2 g 5-(6)-methyl-2-(2-pyridyl)-benzimidazole
  0.07 g tartrazine
  60 ml aqueous citrate buffer (containing 13.6 g citric acid and 6 g sodium hydroxide)
  40 ml ethanol
Solution II:
  3.2 g diisopropylhydroperoxide
  100 ml toluene The resulting test paper discolors into green to blue-green upon dipping in blood-containing urine.

EXAMPLE 5

Filter paper MN 215 is impregnated according to Example 1 with the following solutions one after the other and dried:
Solution I:
  4 g polyvinylpyrrolidone
  1 g dioctylsodiumsulphosuccinate
  0.05 g o-tolidinedihydrochloride
  0.07 g tartrazine
  60 ml buffer (see Example 4)
  40 ml ethanol
Solution II:
  3.2 g cumolhydroperoxiae
  0.2 g 5,6-dimethyl-2-(2-pyridyl)-benzimidazole
  100 ml toluene The resulting test paper discolors into green to blue-green upon immersion in blood-containing urine.

EXAMPLE 6

Filter paper MN 215 is impregnated according to Example 1 with the following solutions one after the other and dried:

Solution I:
  5 g polyvinylpyrrodone
  2 g dioctylsodiumsulphosuccinate
  0.07 g tartrazine
  0.2 g 5-(6)-nitro-2-(2-pyridyl)-benzimidazole
  3.2 g 2,5-dimethylhexane-2,5-dihydroperoxide
  60 ml buffer (see Example 4)
  40 ml ethanol Solution II:
  0.5 g 3,3',5,5'-tetramethylbenzidine
  100 ml toluene The resulting test paper discolors into green to blue-green upon immersion in blood-containing urine.

The relative amounts of the active components can be subject to considerable variation. Selection of effective amounts of the various materials is within the skill of the art.

Other compounds within the scope of the general formula can be substituted for those exemplified to obtain results within the scope of this invention.

I claim:

1. In a method of detecting blood or other peroxidatively active substances in body fluids and excretion products by employing an absorbent carrier testing zone, dipping it into said body fluids or excretion products, and observing the color change, wherein the carrier is impregnated with a composition comprising a chromogen, an organic hydroperoxide oxidizing agent, a surface-active agent and an activator, the improvement which comprises employing as the activator 2-(2-pyridyl)-benzimidazole.

2. An article adapted to detect blood or other peroxidatively active substances in body fluids and excretion products comprising a carrier impregnated with a chromogen, a hydroperoxide, a surface-active agent and an activator wherein the activator is 2-(2-pyridyl)-benzimidazole.

* * * * *